United States Patent [19]

Pohmer et al.

[11] Patent Number: 5,414,102
[45] Date of Patent: May 9, 1995

[54] FLUORINATED CARBOXYLIC ACID ESTERS OF PHOSPHONO- AND PHOSPHINOCARBOXYLIC ACIDS CONTAINING ACRYLATE AND/OR METHACRYLATE GROUPS

[75] Inventors: Klaus Pohmer, Köln; Rainer Weber, Odenthal; Hans-Dieter Block; Hans-Heinrich Moretto, both of Leverkusen, all of Germany

[73] Assignee: Bayer Aktiengesellschaft, Leverkusen

[21] Appl. No.: 172,751

[22] Filed: Dec. 27, 1993

[30] Foreign Application Priority Data

Jan. 14, 1993 [DE] Germany .................. 43 00 799.6

[51] Int. Cl.⁶ .............. C07C 9/02; C07C 269/00; C07C 229/00
[52] U.S. Cl. .................. 558/45; 558/166; 558/169; 558/170; 558/172; 558/173; 558/175; 558/180; 558/196; 558/198; 558/201; 558/203; 558/204; 558/21; 558/207; 560/25; 560/29; 560/33; 560/45; 560/49; 560/60; 560/81; 560/87; 560/88; 560/105; 560/113; 560/160; 560/171; 560/180
[58] Field of Search .............. 558/45, 166, 169, 170, 558/172, 173, 175, 180, 196, 198, 201, 203, 204, 214, 207; 560/25, 29, 33, 45, 49, 60, 81, 87, 88, 105, 113, 160, 171, 180

[56] References Cited

U.S. PATENT DOCUMENTS 4,602,092  7/1986  Thottathil et al. ............... 548/112

FOREIGN PATENT DOCUMENTS 238825   9/1987  European Pat. Off.
2424243  11/1975 Germany.
2439281  2/1976  Germany.

Primary Examiner—José G. Dees
Assistant Examiner—Dwayne C. Jones
Attorney, Agent, or Firm—Connolly & Hutz

[57] ABSTRACT

The present invention relates to fluorinated carboxylic acid esters of phosphonocarboxylic acids containing acrylate and/or methacrylate groups, their use as waterproofing or oil-repellency agents, and a method for their preparation.

6 Claims, No Drawings

FLUORINATED CARBOXYLIC ACID ESTERS OF PHOSPHONO- AND PHOSPHINOCARBOXYLIC ACIDS CONTAINING ACRYLATE AND/OR METHACRYLATE GROUPS

The present invention relates to fluorinated carboxylic acid esters of phosphonocarboxylic acids containing acrylate and/or methacrylate groups, their use as waterproofing and/or oil-repellency agents, and a method for their preparation.

Compounds containing perfluoroalkyl groups are widely used in impregnation agents in industry due to their waterproofing and oil-repellency properties (see Ullmann, Enzyklopädie der technischen Chemie, Fourth Edition, 1976, Volume 11, page 644; and ibid, Fifth Edition, 1988, Volume A11, pages 373-374). Typical applications comprise their use as an impregnation agent for waterproofing and imparting oil-repellency to textiles (see Ullmann, Enzyklopädie der technischen Chemie, Fourth Edition, 1983, Volume 23, page 87), leather (see Ullmann, Enzyklopädie der technischen Chemie, Fourth Edition, 1978, Volume 16, page 168) and paper (see J. N. Meußdoerffer and H. Niederprüm, Chemikerzeitung 104 (1980) 45-52).

Examples of proofing agents such as these comprise alcohols and acrylates containing perfluoro groups, or their polymer dispersions (see J. N. Meußdoerffer and H. Niederprüm, Chemikerzeitung 104 (1980) 45-52; and Ullmann, Enzyklopädie der technischen Chemie, Fourth Edition, 1983, Volume 23, page 87). Routes for their synthesis are described by J. N. Meußdoerffer and H. Niederprüm in Chemikerzeitung 104 (1980) 45-52.

The perfluorinated compounds used as starting materials in the above-mentioned fluorinated surfactants are produced industrially by three different routes:
a) electrochemical fluorination;
b) telomerization of perfluorolefines, particularly tetrafluoroethylene; and
c) oligomerization of tetrafluoroethylene.

The above-mentioned methods of preparing perfluorinated starting materials are very expensive on an industrial scale, which results in high manufacturing costs for the desired chemical compounds containing perfluoro groups.

The object of the invention is to provide modified organic compounds containing fluoro groups which have waterproofing and/or oil-repellency properties, and which can be produced simply and inexpensively.

This object is achieved by means of the fluorinated carboxylic acid esters of phosphono- or phosphinocarboxylic acids containing acrylate and/or methacrylate groups according to the invention.

The present invention relates to fluorinated carboxylic acid esters of phosphono- or phosphinocarboxylic acids containing acrylate and/or methacrylate groups, of general formula (I):

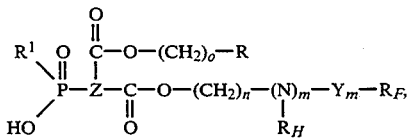

(I)

where
$R^1$ is a hydroxyl group, a methyl group, an ethyl group or a phenyl radical,
$R_F$ is a linear or branched fluoroalkyl radical with 1 to 18 carbon atoms, or a fluorinated, branched or linear monomeric ether or polyether with 1 to 18 carbon atoms,
$R_H$ is a linear or branched alkyl radical with 1 to 10 carbon atoms,
R is an acrylate group of structure

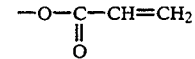

or a methacrylate group of structure

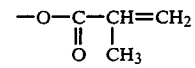

Y represents a

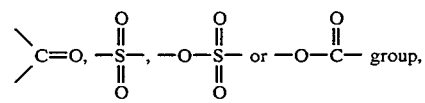

Z represents a linear or branched alkanetriyl radical (trivalent hydrocarbon radical) with 1 to 20 carbon atoms, or
a linear or branched alkanetriyl radical with 1 to 20 carbon atoms, interrupted by amino groups which may themselves contain $C_1$ to $C_{10}$ alkyl groups or aryl groups as substituents, or
a linear or branched alkanetriyl radical with 1 to 20 carbon atoms with one or more substituent groups of structure —$COR^2$,
or a linear or branched alkanetriyl radical with 1 to 20 carbon atoms with one or more substituent groups of structure —$PO_2HR^1$, where $R^1$ has the same meaning as above,
m may be 0 or 1,
n is an integer from 0 to 6,
o is an integer from 0 to 6, and
$R^2$ represents a hydroxyl radical, or a radical of structure

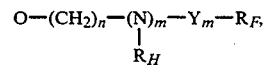

or a radical of structure O—$(CH_2)_o$—R, or
a linear or branched alkoxy radical with 1 to 30 carbon atoms, where n, m, o, $R_H$, $R_F$, R and Y have the same meaning as above,
and their salts.

The fluorinated carboxylic acid esters of phosphono- or phosphinocarboxylic acids containing acrylate and/or methacrylate groups are preferably those in which $R_F$ is a linear or branched fluoroalkyl radical with 3 to 10 carbon atoms.

Fluorinated carboxylic acid esters of phosphono- or phosphinocarboxylic acids containing acrylate and/or methacrylate groups, in which $R_H$ represents an alkyl radical with one or two carbon atoms, are preferred.

Fluorinated carboxylic acid esters of phosphono- or phosphinocarboxylic acids containing acrylate and/or methacrylate groups, in which n is one or two, are particularly preferred.

Fluorinated carboxylic acid esters of phosphono- or phosphinocarboxylic acids containing acrylate and/or methacrylate groups, in which o is one or two, are particularly preferred.

Fluorinated carboxylic acid esters of phosphono- or phosphinocarboxylic acids containing acrylate and/or methacrylate groups, in which m is equal to one, are particularly preferred.

For example, particularly preferred fluorinated carboxylic acid esters of phosphono- or phosphinocarboxylic acids containing acrylate and/or methacrylate groups have the following structure:

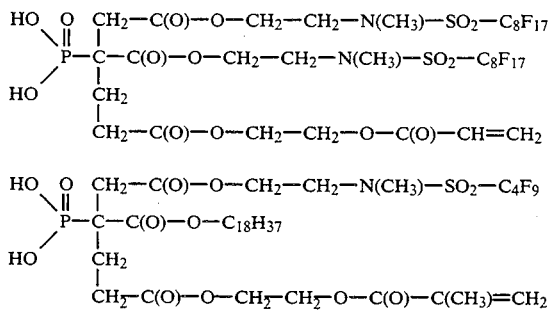

The radicals listed below are particularly preferred:
Examples of $R_F$:

$CF_3—(CF_2)_2—$
$CF_3—(CF_2)_3—$
$CF_3—(CF_2)_5—$
$CF_3—(CF_2)_6—$
$CF_3—(CF_2)_7—$
$CF_3—(CF_2)_{11}—$
$C_6F_5—$
$CF_3C_6F_4—$
$H—(CF_2)_6—$
$H—(CF_2)_2—O—$
$CF_3—CHF—CF_2—O—$
$CF_3—CF_2—CF_2—O—CF(CF_3)—$
$CF_3—CF_2—[CF_2—O—CF(CF_3)]_2—$
$CF_3—CF_2—[CF_2—O—CF(CF_3)]_3—$

Examples of Z:

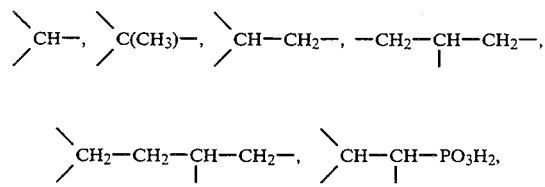

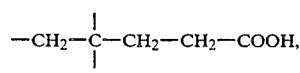

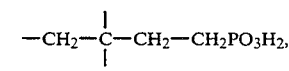

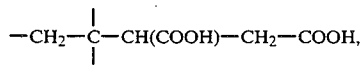

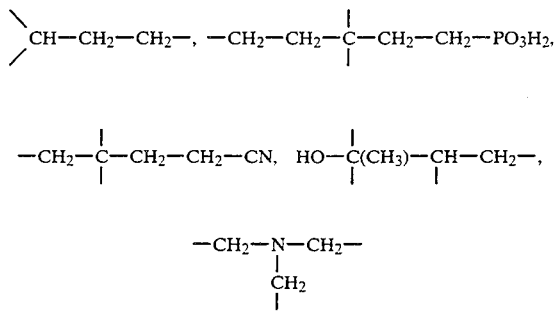

The fluorinated carboxylic acid esters of phosphono- or phosphinocarboxylic acids containing acrylate and/or methacrylate groups according to the invention may be prepared by multi-stage synthesis, employing esterification reactions of the corresponding phosphono- or phosphinocarboxylic acids or their salts with alcohols containing fluoro groups and hydroxyfunctional acrylic acid or methacrylic acid derivatives:

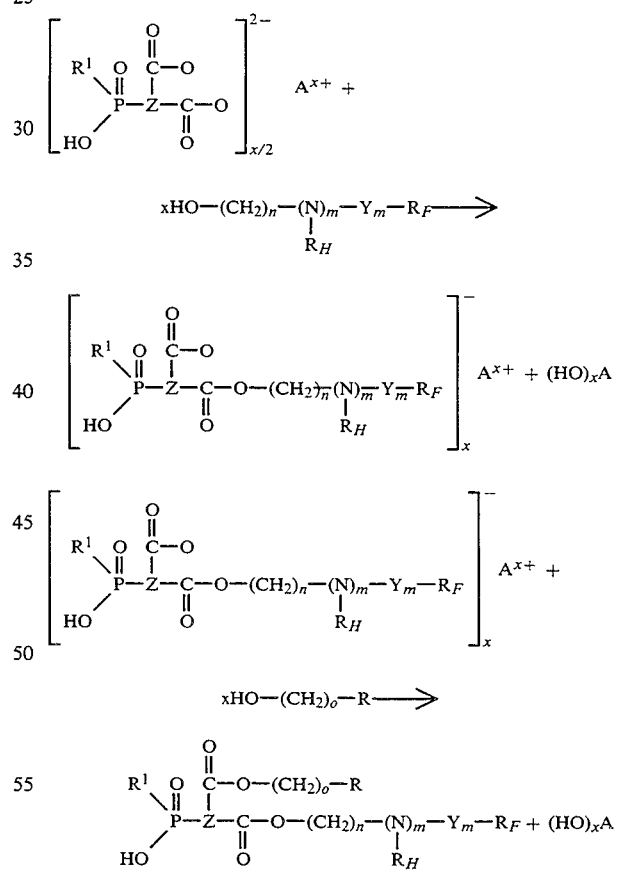

where
$R^1$, R, $R_F$, $R_H$, Y, Z, m, n and o have the same meaning as above,
A is a hydrogen cation, an ammonium cation or a monovalent or polyvalent metal cation, and
x is an integer which corresponds to the charge of the cation A.

The present invention also relates to the use of the fluorinated carboxylic acid esters of phosphono- or phosphinocarboxylic acids containing acrylate and/or methacrylate groups according to the invention as waterproofing agents and/or oil-repellency agents.

Due to the waterproofing and oil-repellency properties of the compounds according to the invention, they may be used as impregnating agents in various areas of application, whereby the compounds according to the invention may be applied as such or in the form of polymer dispersions, for example.

For example, the compounds according to the invention may be used on natural and synthetic fibres (e.g. for textiles, carpets or awnings) to repel water, grease, oil and/or dirt.

The compounds according to the invention may also be used on paper and cardboard (e.g. for packaging or fleeces) to repel water, grease, oil and/or dirt.

Moreover, the compounds according to the invention may be used on leather (e.g. for upholstery, shoes or clothing) to repel water, grease, oil and/or dirt.

The compounds according to the invention may also be used on ceramics (e.g. tiles), on natural or artificial stone (e.g. sandstone), on wood (e.g. the wooden cladding of facades) and on plastics (e.g. polyesters) for impregnation against water, grease, oil, dirt, algae growth and/or weathering.

The invention will be described in more detail by means of the following examples.

EXAMPLES

Example 1

N-(2-hydroxyethyl)-N-methyl-perfluorooctyl sulphonamide (0.4 mole/223 g) was dissolved in 150 ml 4-methyl-pentane-2-one in a three-necked flask fitted with a stirrer and a water trap, and 0.5 ml concentrated sulphuric acid was added.

This solution was heated to about 116° C. 2-phosphonobutane1,2,4-tricarboxylic acid (0.2 mole/54 g) dissolved in 54 g water was then slowly added. After the addition was complete, the reaction mixture was refluxed with stirring until the entire amount of water (61.2 ml) had been distilled off.

Hydroxyethyl acrylate (0.2 mole/23.2 g) was then slowly added, followed by stirring under reflux until the entire amount of water (3.6 ml) had been distilled off from the reaction mixture.

After the reaction was complete, the solvent was distilled off at 70° C. and 70 mbar, and the product obtained was completely dried. The yield of 2-phosphonobutane-1,2,4-tricarboxylic acid which was triple-esterified with two equivalents of N-(2-hydroxyethyl)-N-methyl-perfluorooctyl sulphonamide and one equivalent of hydroxyethyl acrylate was 277 g (95.8% theoretical).

Example 2

N-(2-hydroxyethyl)-N-methyl-perfluorobutyl sulphonamide (0.2 mole/71 g) was dissolved in 150 ml 4-methyl pentane-2-one in a three-necked flask fitted with a stirrer and a water trap, and concentrated sulphuric acid (0.5 ml) was added. This solution was heated to about 116° C. 2-phosphonobutane-1,2,4-tricarboxylic acid (0.2 mole/54 g) dissolved in 54 g water was then slowly added. After the addition was complete, the reaction mixture was refluxed with stirring until the entire amount of water (57.6 ml) had been distilled off.

Octadecanol (0.2 mole/54 g) dissolved in 50 ml 4-methyl-pentane-2-one was then slowly added, followed by stirring under reflux until the entire amount of water (3.6 ml) had been distilled off from the reaction mixture.

Hydroxyethyl methacrylate (0.2 mole/26 g) was then slowly added, followed by stirring under reflux until the entire amount of water (3.6 ml) had been distilled off from the reaction mixture.

After the reaction was complete, the solvent was distilled off at 70° C. and 70 mbar, and the product obtained was completely dried. The yield of 2-phosphonobutane-1,2,4-tricarboxylic acid which was triple-esterified with one equivalent each of N-(2-hydroxyethyl)-N-methyl-perfluorobutyl sulphonamide, octadecanol and hydroxyethyl methacrylate was 180 g (92.5% theoretical).

What is claimed is:

1. Fluorinated carboxylic acid esters of phosphono- or phosphinocarboxylic acids containing acrylate and/or methacrylate groups, of formula (I)

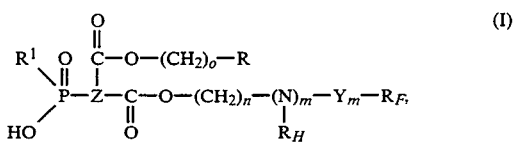

wherein:

$R^1$ is a hydroxyl group, a methyl group, an ethyl group or a phenyl radical, $R_F$ is a linear or branched fluoroalkyl radical with 1 to 18 carbon atoms, or a fluorinated branched or linear monomeric ether or polyether with 1 to 18 carbon atoms, $R_H$ is a linear or branched alkyl radical with 1 to 10 carbon atoms, R is an acrylate group of structure

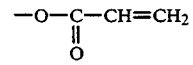

or a methacrylate group of structure

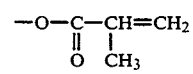

Y represents a

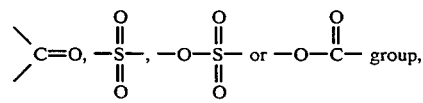 group,

Z represents a linear or branched alkanetriyl radical (trivalent hydrocarbon radical) with 1 to 20 carbon atoms, or a radical of the formula

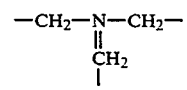

or a linear or branched alkanetriyl radical with 1 to 20 carbon atoms with one or more substituent groups of structure $COR^2$, or a linear or branched alkanetriyl radical with 1 to 20 carbon atoms with one or more substituent groups of structure $-PO_2HR^1$, where $R^1$ has the same meaning as above, m is 0 or 1, n is an integer from 0 to 6, is an integer from 0 to 6, and $R^2$ represents a hydroxyl radical or a radical of structure

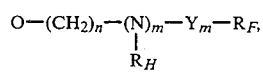

or a radical of structure $O-(CH_2)_o-R$, or a linear or branched alkoxy radical with 1 to 30 carbon atoms, where n, m, o, $R_H$, $R_F$ and Y have the same meaning as above, and their salts.

2. Compounds according to claim 1, wherein $R_F$ is a linear or branched fluoroalkyl radical with 3 to 10 carbon atoms.

3. Compounds according to claim 1, wherein $R_H$ represents an alkyl radical with one or two carbon atoms.

4. Compounds according to claim 1, wherein n is one or two.

5. Compounds according to claim 1, wherein o is one or two.

6. Compounds according to claim 1, wherein m is equal to one.

* * * * *